United States Patent

Sturtz et al.

[11] 4,102,830
[45] Jul. 25, 1978

[54] DIOL-PHOSPHONATES AS FLAME-RETARDANTS IN POLYURETHANE FOAM

[75] Inventors: Georges L. Sturtz, Brest; Serge L. Lecolier, Janville sur Juine; Jean-Claude Clement, Brest; Jean Marie Biehler, Brunstatt, all of France

[73] Assignee: Societe Nationale des Poudres et Explosifs, France

[21] Appl. No.: 801,837

[22] Filed: May 31, 1977

Related U.S. Application Data

[62] Division of Ser. No. 570,413, Apr. 22, 1975, Pat. No. 4,052,487.

[30] Foreign Application Priority Data

May 13, 1974 [FR] France .................. 74 16477

[51] Int. Cl.² .............................................. C08G 18/32
[52] U.S. Cl. .................................................. 521/165
[58] Field of Search .............. 260/2.5 AJ, 2.5 AR, 260/2.5 AQ

[56] References Cited

U.S. PATENT DOCUMENTS 3,076,010  1/1963  Beck ........................... 260/2.5 AJ
3,235,517  2/1966  Beck ........................... 260/2.5 AJ
3,294,710  12/1966 Rosenberg ..................... 260/2.5 AJ
3,674,748  7/1972  Iliopulos ...................... 260/2.5 AJ
4,052,487  10/1977 Sturtz ......................... 260/2.5 AJ

*Primary Examiner*—C. Warren Ivy
*Attorney, Agent, or Firm*—Bucknam and Archer

[57] ABSTRACT

The novel diol-phosphonates of the formula:

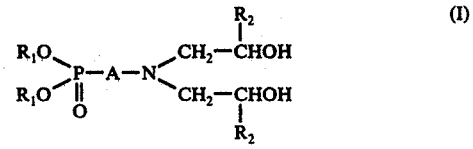

in which $R_1$ is alkyl with 1 to 4 carbon atoms, $R_2$ is hydrogen, methyl, or ethyl, and A is $-CH_2-CH_2-CH_2-$, or

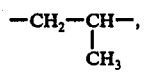

are useful as flameproofing additives in polyurethane foams.

7 Claims, No Drawings

DIOL-PHOSPHONATES AS FLAME-RETARDANTS IN POLYURETHANE FOAM

This is a division, of application Ser. No. 570,413, filed Apr. 22, 1975, now U.S. Pat. No. 4,052,487.

The present invention relates to certain novel diol-phosphonates, and to their use in flameproofing polyurethane foams.

It is known that phosphorus-containing derivatives reduce the inflammability of products into which they are introduced. Phosphorus can be added in the form of unreactive compounds to polymers or copolymers; however, in this case, the phosphorus-containing compounds tend to exude from the polymer. It is therefore preferable to introduce phosphorus into a polymeric material, by employing a phosphorus-containing monomer in the copolymerization or copolycondensation reactions used to form the polymeric material.

In order to flameproof polyurethane foams, it has already been proposed to use diol-phosphonates of the formula

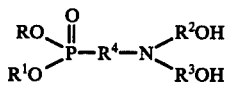

in which R and $R^1$ are alkyl, $R^2$ and $R^3$ are alkylene and $R^4$ is methylene. These compounds may be prepared by a Mannich reaction between a dialkyl phosphite, a dialkanolamine and an aldehyde or a ketone (U.S. Pat. No. 3,076,010). A compound of this type is commercially available under the trade name "Fyrol 6". It is prepared by means of a Mannich reaction between diethyl phosphite, formaldehyde and diethanolamine, and has the formula

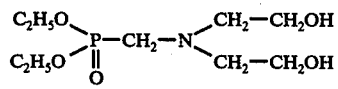

Compounds of this type, however, possess the disadvantage of undergoing a reverse Mannich reaction, a so-called "retro Mannich reaction", when in monomeric form or when incorporated into a polymer. This manifests itself in storage and processing difficulties and in a deterioration of the mechanical properties of polyurethane foams prepared with these compounds.

We have now developed certain novel diolphosphonates which do not possess this disadvantage and which enable a better flameproofing effect to be obtained.

The novel compounds according to the present invention have the following general formula:

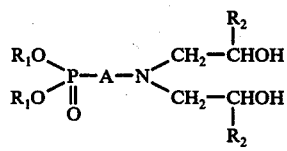

in which $R_1$ is an alkyl group with 1 to 4 carbon atoms, $R_2$ is hydrogen, methyl, or ethyl, and A is $-CH_2-CH_2-CH_2-$ or

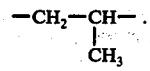

A compound which has proved particularly valuable is diethyl 3-[bis-(2-hydroxy-ethyl)-amino]-propyl-phosphonate, and another preferred compound is diethyl 2-[bis-(2-hydroxy-ethyl)-amino-]-2-methylethyl phosphonate.

The compounds of the formula I in which A is a trimethylene radical, $-(CH_2)_3-$, can be prepared in accordance with the following reaction schemes (a), (b) and (c).

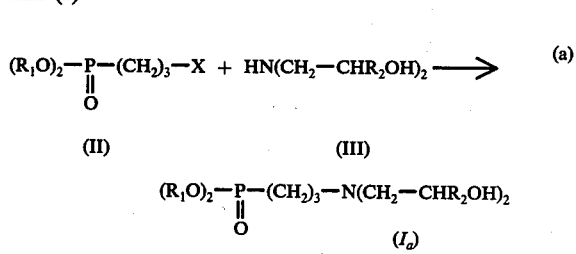

In this scheme X is a chlorine or bromine atom, and $R_1$ and $R_2$ have the meanings given above.

The phosphonates II used in process (a) may be prepared by the reaction of a trialkyl phosphite with a dihalogeno-alkane, in accordance with known methods (Parfentjew and Schafiew, Trudy Usbekak Univ. Sbornik Rabot Chim., 1939, 15, 87; C.A., 1941, 3963; and T. R. Fukuto and R. L. Metcalf, J. Amer. Chem. Soc., 1959, 81, 372-7). These methods possess the disadvantage of giving only average yields, even in the presence of an excess of the halogenated derivative, the halogen being only slightly activated in this type of compound. The action of a dialkanolamine III, preferably in the presence of triethylamine, on the phosphonates II leads to the diol-phosphonates $I_a$ as shown in scheme (a).

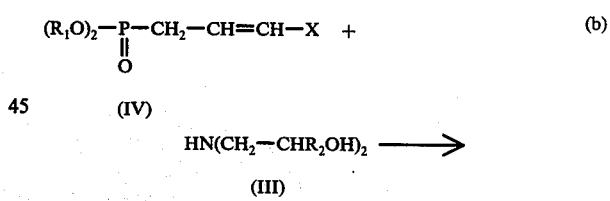

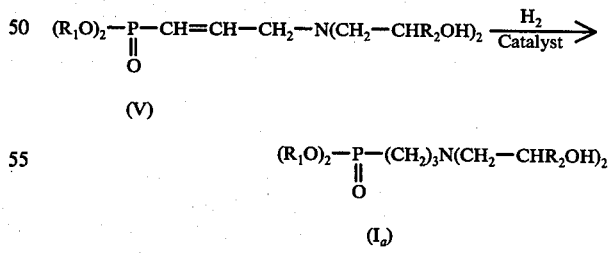

In this scheme X is a chlorine or bromine atom and $R_1$ and $R_2$ have the meanings given above.

The β-ethylenic-γ-halogenated-phosphonates IV have been described by Laviolle, Sturtz and Normant (Bull.Soc.Chim., 1967, 4186).

The dialkanolamine III reacts with the phosphonates IV, preferably in the presence of triethylamine, in a manner analogous to the reaction that occurs with phosphonates II, forming derivatives V, which are thereafter catalytically reduced to form diolphosphonates $I_a$. This hydrogenation is preferably carried out using Pd/C at atmospheric pressure, or in an autoclave under a few atmospheres and at ambient temperature.

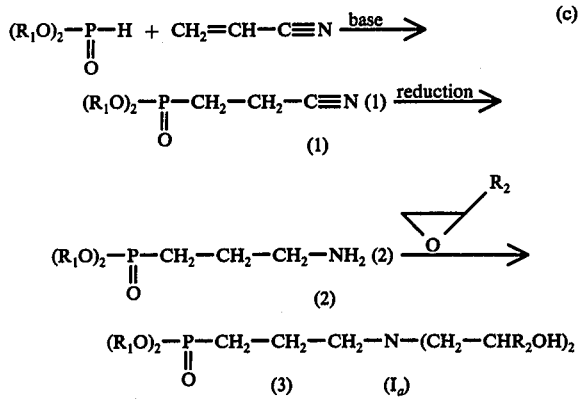

In this scheme $R_1$ and $R_2$ have the meanings given above.

The compounds of formula I in which A is

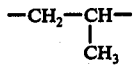

can be prepared in accordance with the following scheme:

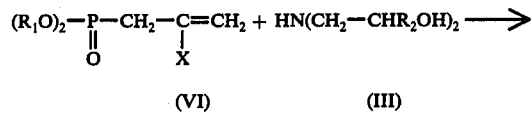

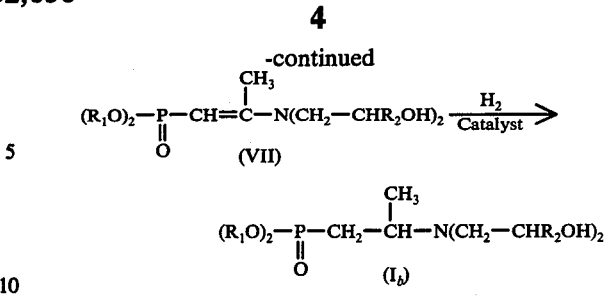

The phosphonates VI are described in U.S. Pat. No. 2,827,475. The reaction of the dialkanolamine III with the phosphonate VI is advantageously carried out in the presence of triethylamine. The compounds VII are then reduced by catalytic hydrogenation to form diol-phosphonates $I_b$ under fairly vigorous conditions (preferably using a pressure of at least 70 bars and a temperature of about 70° C).

The following Examples describing the preparation of compounds of the invention are given by way of illustration only.

EXAMPLES 1 to 8

In Examples 1 to 8, diol-phosphonates of formula $I_a$ were prepared in accordance with general reaction procedure (1) or (2) described below. The starting materials, reaction procedure, product and yield obtained are summarised in Table 1 below. (1) 100 cm³ of an alcohol $R_1$OH, 0.1 mole of a phosphonate II, 0.2 mole of triethylamine and 0.2 mole of a dialkanolamine III were heated under reflux. The mixture was left under reflux for 6 to 7 hours in the case of brominated derivatives II and for 24 hours in the case of chlorinated derivatives II. (2) The same procedure as described under (1) was employed but a phosphonate IV was used in place of the phosphonate II.

Thereafter, after filtering off the triethylammonium halide precipitate, the crude product was hydrogenated in the alcoholic solution in which it was prepared (using 5% by weight of 10% Pd/C, at 25° C for 2 hours under a pressure of 10 bars, or at atmospheric pressure).

TABLE 1

(Diol-phosphonates $I_a$)

| Example No. | Reaction procedure | Starting phosphonate | Amine | Product obtained | Compound No. | Yield % |
|---|---|---|---|---|---|---|
| 1 | (1) | (EtO)$_2$—P(O)—(CH$_2$)$_3$—Br | HN(CH$_2$CH$_2$OH)$_2$ | (EtO)$_2$—P(O)—(CH$_2$)$_3$—N(CH$_2$CH$_2$OH)$_2$ | 1 | 82 |
| 2 | (1) | (EtO)$_2$—P(O)—(CH$_2$)$_3$Br | HN(CHOHCH$_3$)$_2$ | (EtO)$_2$—P(O)—(CH$_2$)$_3$—N(CH$_2$CHOHCH$_3$)$_2$ | 2 | 88 |
| 3 | (1) | (isoPrO)$_2$—P(O)(CH$_2$)$_3$Br | HN(CH$_2$CH$_2$OH)$_2$ | (isoPrO)$_2$—P(O)—(CH$_2$)$_3$—N(CH$_2$CH$_2$OH)$_2$ | 3 | 91 |
| 4 | (1) | (isoPrO)$_2$—P(O)(CH$_2$)$_3$Br | HN(CH$_2$CHOHCH$_3$)$_2$ | (isoPrO)$_2$P(O)—(CH$_2$)$_3$—N(CH$_2$CHOHCH$_3$)$_2$ | 4 | 88 |
| 5 | (1) | (EtO)$_2$—P(O)(CH$_2$)$_3$Cl | HN(CH$_2$CH$_2$OH)$_2$ | (EtO)$_2$—P(O)—(CH$_2$)$_3$—N(CH$_2$CH$_2$OH)$_2$ | 1 | 56 |
| 6 | (1) | (EtO)$_2$—P(O)—(CH$_2$)$_3$Cl | HN(CH$_2$CHOHCH$_3$)$_2$ | (EtO)$_2$—P(O)—(CH$_2$)$_3$—N(CH$_2$CHOHCH$_3$)$_2$ | 2 | 63 |
| 7 | (2) | (EtO)$_2$—P(O)—CH$_2$—CH=CHCl | HN(CH$_2$CH$_2$OH)$_2$ | (EtO)$_2$—P(O)—(CH$_2$)$_3$—N(CH$_2$CH$_2$OH)$_2$ | 1 | 72 |

TABLE 1-continued (Diol-phosphonates I_a)

| Example No. | Reaction procedure | Starting phosphonate | Amine | Product obtained | Compound No. | Yield % |
|---|---|---|---|---|---|---|
| 8 | (2) | $(isoPrO)_2\overset{O}{\underset{\|}{P}}-CH_2-CH=CHCl$ | $HN(CH_2CH_2OH)_2$ | $(isoPrO)_2\overset{O}{\underset{\|}{P}}-(CH_2)_3N(CH_2CH_2OH)_2$ | 3 | 69 |

EXAMPLES 9 to 15

Diol-phosphonates of formula $I_b$ were prepared in accordance with the following general reaction procedure. The starting materials, product and yield are summarised in Table 2 below.

100 cm³ of an alcohol $R_1OH$, 0.1 mole of a phosphonate VI, 0.2 mole of triethylamine and 0.2 mole of a dialkanolamine III were heated under reflux. The mixture was left under reflux for 6 to 7 hours in the case of brominated derivatives VI and for 24 hours in the case of chlorinated derivatives VI.

After cooling and filtering off the triethylammonium halide precipitate, the excess alcohol and triethylamine were driven off under reduced pressure. The residue was hydrogenated over Pd/C in the alcohol $R_1OH$ at 70° C for 14 hours under 80 bars. After filtering off the Pd/C and evaporating the alcohol, the residue was taken up in water and in $CHCl_3$. The residual starting products were extracted at pH 1 and the diol-phosphonate was extracted at pH 10.

Certain characteristics of the products obtained are given below, together with some spectral data.

Diethyl 3-[bis-(2-hydroxy-ethyl)-amine]-propyl-phosphonate (1)

Empirical formula $C_{11}H_{26}NO_5P$: Oil $n_D^{22}= 1.4642$.
IR = $\nu_{OH}$ = 3,382 cm⁻¹: $\nu_{P=O}$= 1,225 cm⁻¹. NMR ($CCl_4$, δ in ppm).

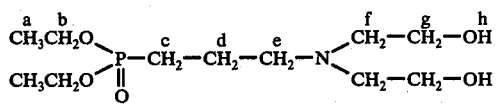

$6H_a$ at 1.3 (triplet); $4H_b$ at 4.05 (quintuplet); $2H_c + 2H_d$ at 1.7 (hump); $2H_e + 4H_f$ at 2.56 (triplet); $4H_g$ at 3.05 (triplet); and $2H_h$ at 4.5 (singlet).

Diethyl 3-[bis-(2-hydroxy-propyl)-amino]-propyl-phosphonate (2)

Empirical formula $C_{13}H_{30}NO_5P$: Oil $n_D^{22} = 1.4583$.
IR = $\nu_{OH}$ = 3,340 cm⁻¹: $\nu_{P=o}$= 1,220 cm⁻¹. NMR ($CCl_4$, δ in ppm).

Table 2

(Diol-phosphonates $I_b$)

| Example No. | Starting phosphonate | Amine | Product obtained | Compound No. | Yield % |
|---|---|---|---|---|---|
| 9 | $(EtO)_2-\underset{O}{\overset{\|}{P}}-CH_2-\underset{Br}{\overset{\|}{C}}=CH_2$ | $HN(CH_2CH_2OH)_2$ | $(EtO)_2-\underset{O}{\overset{\|}{P}}-CH_2-\underset{CH_3}{\overset{\|}{CH}}-N(CH_2CH_2OH)_2$ | 5 | 81 |
| 10 | $(EtO)_2-\underset{O}{\overset{\|}{P}}-CH_2-\underset{Br}{\overset{\|}{C}}=CH_2$ | $HN(CH_2CHOHCH_3)_2$ | $(EtO)_2-\underset{O}{\overset{\|}{P}}-CH_2-\underset{CH_3}{\overset{\|}{CH}}-N(CH_2CHOHCH_3)_2$ | 6 | 91 |
| 11 | $(isoPrO)_2-\underset{O}{\overset{\|}{P}}-CH_2-\underset{Br}{\overset{\|}{C}}=CH_2$ | $HN(CH_2CH_2OH)_2$ | $(isoPrO)_2-\underset{O}{\overset{\|}{P}}-CH_2-\underset{CH_3}{\overset{\|}{CH}}-N(CH_2CH_2OH)_2$ | 7 | 88 |
| 12 | $(isoPrO)_2-\underset{O}{\overset{\|}{P}}-CH_2-\underset{Br}{\overset{\|}{C}}=CH_2$ | $HN(CH_2CHOHCH_3)_2$ | $(isoPrO)_2\overset{O}{\underset{\|}{P}}-CH_2-\underset{CH_3}{\overset{\|}{CH}}-N(CH_2CHOHCH_3)_2$ | 8 | 83 |
| 13 | $(EtO)_2-\underset{O}{\overset{\|}{P}}-CH_2-\underset{Cl}{\overset{\|}{C}}=CH_2$ | $HN(CH_2CH_2OH)_2$ | $(EtO)_2-\underset{O}{\overset{\|}{P}}-CH_2-\underset{CH_3}{\overset{\|}{CH}}-N(CH_2CH_2OH)_2$ | 5 | 72 |
| 14 | $(EtO)_2-\underset{O}{\overset{\|}{P}}-CH_2-\underset{Cl}{\overset{\|}{C}}=CH_2$ | $HN(CH_2CHOHCH_3)_2$ | $(EtO)_2-\underset{O}{\overset{\|}{P}}-CH_2-\underset{CH_3}{\overset{\|}{CH}}-N(CH_2CHOHCH_3)_2$ | 6 | 75 |
| 15 | $(BuO)_2-\underset{O}{\overset{\|}{P}}-CH_2-\underset{Br}{\overset{\|}{C}}=CH_2$ | $HN(CH_3CH_2OH)_2$ | $(BuO)_2-\underset{O}{\overset{\|}{P}}-CH_2-\underset{CH_3}{\overset{\|}{CH}}-N(CH_2CH_2OH)_2$ | 9 | 63 |

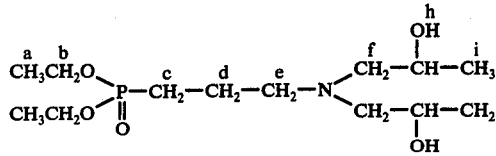

6H$_a$ at 1.3 (triplet); 4H$_b$ at 4.02 (quintuplet); 2H$_c$ + 2H$_d$ at 1.7 (hump); 2H$_e$ + 4H$_f$ at 2.38 (multiplet); 2H$_g$ at 3.65 (hump); 2H$_h$ at 4.26 (singlet); and 6H$_i$ at 1.02 (doublet).

Diisopropyl 3-[bis-(2-hydroxy-ethyl)-amino]-propyl-phosphonate (3)

Oil $n_D^{22}$ = 1.4608.
IR = $\nu_{OH}$ = 3,380 cm$^{-1}$: $\nu_{P=O}$ = 1,221 cm$^{-1}$. NMR (CCl$_4$, δ in ppm).

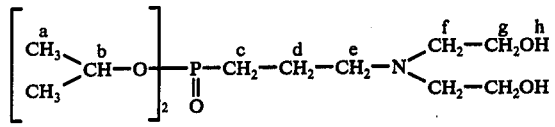

12H$_a$ at 1.35 (doublet); 2H$_b$ + 2H$_h$ at 4.8 (hump); 2H$_c$ + 2H$_d$ at 1.7 (hump); 2H$_e$ + 4H$_f$ at 2.58 (triplet); and 4H$_g$ at 3.51 (triplet).

Diisopropyl 3-[bis-(2-hydroxy-propyl)-amino]-propyl-phosphonate (4)

Oil $n_D^{22}$ = 1.4542.
IR: $\nu_{OH}$ = 3,390 cm$^{-1}$: $\nu_{P=O}$ = 1,230 cm$^{-1}$.
NMR (CCl$_4$, δ in ppm) =

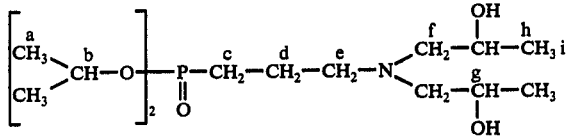

12H$_a$ at 1.33 (doublet); 2H$_b$ + 2H$_h$ at 4.5 (hump); 1H$_e$ + 4H$_f$ at 2.40 (multiplet); 2H$_g$ at 3.70 (hump); and 6H$_i$ at 1.03 doublet).

Diethyl 2-[bis-(2-hydroxy-ethyl)-amino]-2-methyl-ethyl-phosphonate (5)

Empirical formula C$_{11}$H$_{26}$NO$_5$P Oil $n_D^{22}$ = 1.4627.
IR: $\nu_{OH}$ = 3,390 cm$^{-1}$: $\nu_{P=O}$ = 1,215 cm$^{-1}$.
NMR (CCl$_4$, δ in ppm) =

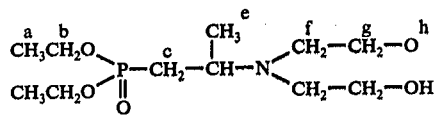

6H$_a$ at 1.4 (triplet); 4H$_b$ at 4.12 (quintuplet); 2H$_c$ at 1.8 (multiplet); 4H$_b$ at 2.56 (multiplet); 4H$_g$+ H$_d$ at 3.48 (multiplet); 2H$_h$ at 4.26 (singlet); and 3H$_c$ at 1.1 (doublet).

Diethyl 2-[bis-(2-hydroxy-propyl)-amino]-2-methyl-ethyl-phosphonate (6)

Oil $n_D^{22}$ = 1.4562.
IR: $\nu_{OH}$ = 3,400 cm$^{-1}$; $\nu_{P=O}$ = 1,221 cm$^{-1}$.
NMR (CCl$_4$, δ in ppm) =

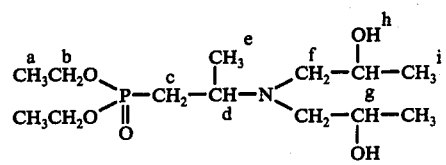

6H$_a$ at 1.32 (triplet); 4H$_b$ + H$_d$ + 2H$_g$ at 4.08 (multiplet); 2H$_c$ at 2.8 (multiplet); 3H$_c$ + 6H$_i$ at 1.05 (appearance of doublet); 4H$_f$ at 2.35 (multiplet); and 2H$_h$ at 4.2 (singlet).

Diisopropyl 2-[bis-(2-hydroxy-ethyl)-amino]-2-methyl-ethyl-phosphonate (7)

Empirical formula: C$_{13}$H$_{30}$NO$_5$P: Oil $n_D^{23}$ = 1.4576.
IR = $\nu_{OH}$ = 3,350 cm$^{-1}$: $\nu_{P=O}$ = 1,205 cm$^{-1}$.
NMR (CCl$_4$, δ in ppm)

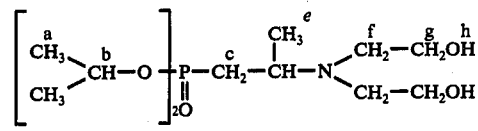

12H$_a$ at 1.35 (doublet); 2H$_b$ at 4.6 (septet); 2H$_c$ at 1.8 (hump); 3H$_e$ at 1.08 (doublet); 4H$_f$ at 2.5 (multiplet); 4H$_g$ + H$_d$ at 3.38 (hump); and 2H$_h$ at 4.25 (singlet).

Diisopropyl 2-[bis-(2-hydroxy-propyl)-amino]-2-methyl-ethyl-phosphonate (8)

Empirical formula C$_{15}$H$_{34}$NO$_5$P: Oil $n_D^{22}$ = 1.4539.
IR = $\nu_{OH}$ = 3,400 cm$^{-1}$: $\nu_{P=O}$ = 1,225 cm$^{-1}$.
NMR (CCl$_4$, δ in ppm)

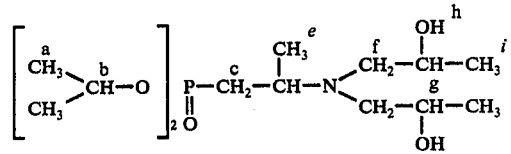

12H$_a$ at 1.28 (doublet); 2H$_b$ at 4.60 (septet); 2H$_c$ at 1.8 (hump); 3H$_e$ + 6H$_i$ at 1.09 (hump); 4H$_f$ at 2.3 (multiplet); 2H$_g$ + H$_d$ at 3.6 (hump); and 2H$_h$ at 4.2 (singlet).

Dibutyl 2-[bis-(2-hydroxy-ethyl)-amino]-2-methyl-ethyl-phosphonate (9)

Oil $n_D^{22}$ = 1.4531.
IR = $\nu_{OH}$ = 3,370 cm$^{-1}$: $\nu_{P=O}$ = 1,220 cm$^{-1}$.
NMR (CCl$_4$, in ppm)

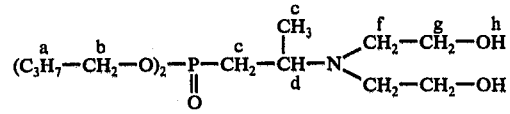

$14H_a + 3H_e + 2H_c$ at 1 and 1.6 (humps); $4H_b$ at 4 (multiplet); $H_d + 4H_g$ at 3.48 (appearance of triplet); $4H_f$ at 2.57 (triplet); and $2H_h$ at 4.32 (singlet).

The flameproofing action of the compounds according to the invention in polyurethane foams has been demonstrated by means of the following tests:

Rigid polyurethane foams were prepared by polycondensation of diol-phosphonates with diisocyanates under the usual conditions for the preparation of these foams. Toluene diisocyanate (TDI) in the form of a mixture of the 2,4- (80%) and 2,6-(20%) isomers, and 4,4'-diisocyanatodiphenylmethane (MDI) were used as the diisocyanates. The foams were prepared in accordance with the so-called "one-shot process" which consists of reacting the diisocyanate with the diol containing the catalysts (tertiary amines and tin derivatives) and the pore-forming agent.

The procedure was as follows:

0.05 mole of the diol-phosphonate containing 0.1 g of diazabicyclooctane, 0.2 g of "Silicone 9193", approximately 2 g of Freon 11 (in the case of diol-phosphonates derived from diisopropanolamine, 0.1 g of dibutyl-tin dilaurate was also added) were cooled slightly, and then 0.05 mole of the diisocyanate was added whilst stirring vigorously. The foam was then left "to rise". The "cream" times were of the order of 5 to 10 seconds.

The results obtained when the foams thus obtained were brought into contact with a flame are given in Tables 3 and 4 below. In these Tables S.E. denotes self-extinguishing and S.C. denotes slightly combustible. It can be seen that the foams prepared using TDI (Table 3) are more self-extinguishing than those prepared using MDI (Table 4).

TABLE 3

POLYCONDENSATIONS WITH TDI

| Diol-phosphonate | No. | Polyurethane obtained | %P | Type |
|---|---|---|---|---|
| $(EtO)_2P(O)-(CH_2)_3N(CH_2CH_2OH)_2$ | 1 | [tolyl-NH-C(O)-O-CH$_2$CH$_2$-N(-(CH$_2$)$_3$-P(O)(OEt)$_2$)-CH$_2$-CH$_2$-O-C(O)-NH-]$_n$ | 6.8 | S.E. |
| $(EtO)_2P(O)-(CH_2)_3N(CH_2CHOHCH_3)_2$ | 2 | [tolyl-NH-C(O)-O-CH(CH$_3$)-CH$_2$-N(-(CH$_2$)$_3$-P(O)(OEt)$_2$)-CH$_2$-CH(CH$_3$)-O-C(O)-NH-]$_n$ | 6.4 | S.E. |
| $(isoPrO)_2P(O)-(CH_2)_3N(CH_2CH_2OH)_2$ | 3 | [tolyl-NH-C(O)-O-CH$_2$-CH$_2$-N(-(CH$_2$)$_3$-P(O)(OisoPr)$_2$)-CH$_2$-CH$_2$-O-C(O)-NH-]$_n$ | 6.4 | S.E. |
| $(isoPrO)_2P(O)-(CH_2)_3N(CH_2CHOHCH_3)_2$ | 4 | [tolyl-NH-C(O)-O-CH(CH$_3$)-CH$_2$-N(-(CN$_2$)$_3$-P(O)(OisoPr)$_2$)-CH$_2$-CH(CH$_3$)-O-C(O)-NH-]$_n$ | 6 | S.E. |
| $(EtO)_2P(O)-CH_2-CH(CH_3)-N(CH_2CH_2OH)_2$ | 5 | [tolyl-NH-C(O)-O-CH$_2$-CH$_2$-N(-CH(CH$_2$-P(O)(OEt)$_2$)-CH$_3$? )-CH$_2$-CH$_2$-O-C(O)-NH-]$_n$ | 6.8 | S.E. |
| $(EtO)_2P(O)-CH_2-CH(CH_3)-N(CH_2CHOHCH_3)_2$ | 6 | [tolyl-NH-C(O)-O-CH(CH$_3$)-CH$_2$-N(-CH(CH$_3$)-CH$_2$-P(O)(OEt)$_2$)-CH$_2$-CH(CH$_3$)-O-C(O)-NH-]$_n$ | 6.4 | S.E. |
| $(isoPrO)_2P(O)-CH_2-CH(CH_3)-N(CH_2CH_2CH)_2$ | 7 | [tolyl-NH-C(O)-O-CH$_2$-CH$_2$-N(-CH(CH$_3$)-CH$_2$-P(O)(OisoPr)$_2$)-CH$_2$-CH$_2$-O-C(O)-NH-]$_n$ | 6.4 | S.E. |

TABLE 3-continued

POLYCONDENSATIONS WITH TDI

| Diol-phosphonate | No. | Polyurethane obtained | %P | Type |
|---|---|---|---|---|
| $(isoPrO)_2\overset{\underset{\parallel}{O}}{P}-CH_2-\overset{\underset{\mid}{CH_3}}{CH}-N(CH_2CHOHCH_3)_2$ | 8 | $\left[ \text{(tolyl)}-NH-\overset{\underset{\parallel}{O}}{C}-O-\overset{\underset{\mid}{CH_3}}{CH}-CH_2-N(-CH_2-\overset{\underset{\mid}{CH_3}}{CH}-O-\overset{\underset{\parallel}{O}}{C}-NH)-\text{, N-side chain } CH-CH_3, CH_2, (isoPrO)_2P=O \right]_n$ | 6 | S.E. |

TABLE 4

POLYCONDENSATIONS WITH MDI

| Diol-phosphonates No. | Polyurethane obtained | % P | Type |
|---|---|---|---|
| 1 | $\left[ \phi-CH_2-\phi-NH-\overset{\underset{\parallel}{O}}{C}-O-CH_2-CH_2-N(-CH_2-CH_2-O-\overset{\underset{\parallel}{O}}{C}-NH)-, \text{ N-side: }(CH_2)_3, (EtO)_2P=O \right]_n$ | 5.8 | S.E. |
| 2 | $\left[ \phi-CH_2-\phi-NH-\overset{\underset{\parallel}{O}}{C}-O-\overset{\underset{\mid}{CH_3}}{CH}-CH_2-N(-CH_2-\overset{\underset{\mid}{CH_3}}{CH}-O-\overset{\underset{\parallel}{O}}{C}-NH)-, \text{ N-side: }(CH_2)_3, (EtO)_2P=O \right]_n$ | 5.5 | S.E. |
| 3 | $\left[ \phi-CH_2-\phi-NH-\overset{\underset{\parallel}{O}}{C}-O-CH_2-CH_2-N(-CH_2-CH_2-O-\overset{\underset{\parallel}{O}}{C}-NH)-, \text{ N-side: }(CH_2)_3, (isoPrO)_2P=O \right]_n$ | 5.5 | S.E. |
| 4 | $\left[ \phi-CH_2-\phi-NH-\overset{\underset{\parallel}{O}}{C}-O-\overset{\underset{\mid}{CH_3}}{CH}-CH_2-N(-CH_2-\overset{\underset{\mid}{CH_3}}{CH}-O-\overset{\underset{\parallel}{O}}{C}-NH)-, \text{ N-side: }(CH_2)_3, (isoPrO)_2P=O \right]_n$ | 5.2 | S.C. |
| 5 | $\left[ \phi-CH_2-\phi-NH-\overset{\underset{\parallel}{O}}{C}-O-CH_2-CH_2-N(-CH_2-CH_2-O-\overset{\underset{\parallel}{O}}{C}-NH)-, \text{ N-side: }CH-CH_3, CH_2, (EtO)_2P=O \right]_n$ | 5.8 | S.E. |
| 6 | $\left[ \phi-CH_2-\phi-NH-\overset{\underset{\parallel}{O}}{C}-O-\overset{\underset{\mid}{CH_3}}{CH}-CH_2-N(-CH_2-\overset{\underset{\mid}{CH_3}}{CH}-O-\overset{\underset{\parallel}{O}}{C}-NH)-, \text{ N-side: }CH-CH_3, CH_2, (EtO)_2P=O \right]_n$ | 5.5 | S.E. |
| 7 | $\left[ \phi-CH_2-\phi-NH-\overset{\underset{\parallel}{O}}{C}-O-CH_2-CH_2-N(-CH_2-CH_2-O-\overset{\underset{\parallel}{O}}{C}-NH)-, \text{ N-side: }CH-CH_3, CH_2, (isoPrO)_2P=O \right]_n$ | 5.5 | S.C. |

TABLE 4-continued
POLYCONDENSATIONS WITH MDI

| Diol-phosphonates No. | Polyurethane obtained | %P | Type |
|---|---|---|---|
| 8 | [⟨O⟩—CH₂—⟨O⟩—NH—C(=O)—O—CH—CH₂—N(—CH₂—CH(CH₃)—O—C(=O)—NH)—CH(CH₃)] with side chain CH—CH₃, CH₂, (isoPrO)₂P=O ]ₙ | 5.2 | S.C. |

Experiments were also carried out using diol-phosphonates as additives in rigid polyurethane foams. The results obtained are given below, compound No. 1 being used as an example of the diol-phosphonate according to the invention, and the results obtained are compared with those obtained using Fyrol 6, that is to say diethyl [bis-(2-hydroxy-ethyl)-amino]-methyl-phosphonate.

Polyurethane foams were prepared, using the following mixture:

Alcohol: 80 g of TP 440 (trimethylolpropane epoxidised by means of propylene oxide),
isocyanate: 105.5 g of MDI,
blowing agent: 30 g of Forane (Freon II),
catalysts: 0.10 g of DBTL (dibutyl-tin dilaurate) and 1 g of NMM (N-methylmorpholine),
silicone: 1 g of Si 9193 supplied by Messrs. Rhodorsil;
and flameproofing agent: a phosphonate in an amount to provide the P contents indicated in Table 5. The density of the foam thus obtained was approximately 34 g/l.

TABLE 5

| Composition | Phosphorus-containing additive | P content in % |
|---|---|---|
| R | None | 0 |
| 1 | Fyrol 6 | 0.51 |
| 2 | " | 0.96 |
| 3 | " | 1.67 |
| 4 | " | 2.19 |
| 5 | Compound No. 1 | 0.50 |
| 6 | " | 0.70 |
| 7 | " | 0.99 |
| 8 | " | 1.42 |

The flameproof properties of the foams thus prepared were determined by means of the LOI (limiting oxygen index) combustion test.

The mechanical properties, as well as the effect of aging on the mechanical properties, were determined by measuring the corresponding critical pressures of foams of identical density which had been flameproofed by means of 1% of phosphorus.

The tests used were as follows:

LOI: ASTM 2863 test

This test consists of burning a sample of specific dimensions (0.3 × 0.3 × 13 cm) in an atmosphere possessing a defined and adjustable oxygen concentration. The minimum oxygen concentration necessary to cause and maintain combustion is measured. The Limiting Oxygen Index is given by the formula:

$$LOI = \frac{[O_2]}{[O_2] + [N_2]}$$

Compressive Strength: Standard Specification NFT 56,101

This test consists of subjecting a test specimen (5 × 5 × 5 cm) to an increasing pressure between two platens and of determining the corresponding force/crushing diagram. The critical pressure Pc, that is to say the value of the pressure for which the deformation of the sample becomes irreversible, is measured. This value was determined in the expansion direction.

Aging

Two types of aging were carried out:
(a) Aging in a wet atmosphere, by immersion in water for 144 hours at ordinary temperature.
(b) Aging in a dry atmosphere for 22 hours at 140° C.

Results (a) Flameproof properties
Table 6 gives the LOI values measured.

TABLE 6

| Polyurethane foam | %P | LOI |
|---|---|---|
| R | 0 | 0.172 |
| 1 | 0.51 | 0.188 |
| 2 | 0.96 | 0.196 |
| 3 | 1.67 | 0.207 |
| 4 | 2.19 | 0.216 |
| 5 | 0.50 | 0.193 |
| 6 | 0.70 | 0.197 |
| 7 | 0.99 | 0.202 |
| 8 | 1.42 | 0.207 |

This Table shows that the foams which were flameproofed by means of the phosphonate according to the invention possess, for an identical phosphorus content, a better LOI, and thus improved fire-resistance, then the foams which were flameproofed by means of the known phosphonate.

(b) Mechanical properties

The mechanical properties were determined by means of the compressive strength. The critical pressures Pc of the reference foams R and those of the flameproofed foams A and B containing 1% of phosphorus, added respectively in the form of Fyrol 6 and of compound No. 1, were compared. Since the critical pressure Pc depends on the density of the foams, the measurements were made on foams of a particular and identical density. Table 7 gives the values for the critical pressures of the polyurethane foams investigated. Samples of each of the foams R, A and B having two different densities were employed. Table 7 also lists the % variation in the critical pressure of the flameproofed foams A and B compared with the reference foam R, this percentage being defined for foams A and B respectively by the formulae;

$$\frac{(PcA - PcR) \times 100}{PcR} \text{ and } \frac{(PcB - PcR) \times 100}{PcR}.$$

PcR = Pc of foam R
PcA = Pc of foam A
PcB = Pc of foam B

TABLE 7
CRITICAL PRESSURES

| Foam | Density g/l | Critical pressure Po in bars | Variation in Pc in % relative to PcR |
|---|---|---|---|
| R | 35 | 2.2 | — |
| A | 35 | 1.5 | −33 |
| B | 35 | 2.2 | 0 |
| R | 45 | 3.3 | — |
| A | 45 | 2.0 | −37 |
| B | 45 | 3.25 | −1.5 |

Table 7 shows clearly that, for the same density, the critical pressures of the foams R and B are substantially the same, whilst they are considerably less (by approximately 36%) in the case of the foams A. These measurements show that the introduction of compound No. 1 of the invention, which leads to the foam B, does not significantly affect the mechanical properties of the foam.

(c) Aging experiments

In order to investigate the dry and wet aging characteristics of the foams R, A and B, the critical pressures Pc were measured before and after aging, and this made it possible to determine the percentage deterioration in the mechanical properties of the foams which had undergone aging, using the formula:

$$\frac{(Pc_a - Ps_i) \times 100}{Pc_i}$$

$Pc_a$ = critical pressure of the foam after aging
$Po_i$ = critical pressure of the foam before aging Table 8 gives the deteriorations in the mechanical properties of the foams caused by the aging procedures. The measurements were made on foams of density 45 g/l, having a 1% phosphorus content (foams A and B).

TABLE 8
AGING EXPERIMENTS

| | Deterioration in the mechanical properties, in % | |
|---|---|---|
| Foam | Wet aging | Dry aging |
| R | +5 | −6 |
| A | −11 | −8 |
| B | −16 | −9 |

Notes

After wet aging, the reference foam R possessed better mechanical properties. This could arise from the excess isocyanate groups in these formulations, leading to crosslinking reactions under the action of water. In contrast, the mechanical properties of the foams A and B underwent slight deterioration during the 2 types of aging processes.

The deterioration was more marked in the case of wet aging because of the partial hydrolysis of the ester-phosphonate groups leading to phosphonic acids, which in their turn promoted hydrolysis reactions.

Other experiments were carried out which further demonstrated the advantages possessed by the foams flameproofed by means of a phosphonate according to the invention.

(b) Delay in self-ignition

| Epiradiator: 300° C | | |
|---|---|---|
| Foam R | Foam A | Foam B (according to the invention) |
| (Reference foam) | (Containing 1% of Fyrol 6) | (Containing 1% of compound No. 1) |
| 5.2 seconds | 4.7 seconds | 5.6 seconds |

It is seen that the foam according to the invention ignites after a longer period than the reference foam and after a considerably longer period than the foam containing Fyrol.

(e) Fume density

Maximum specific optical density above the sample set alight, as measured in the NBS fume chamber.

$$SOD_{max.} = \frac{V}{AL} \log \frac{I \times 100}{Io}$$

I = light transmitted at the maximum evolution of fumes
Io = light transmitted before setting alight
V/AL = factor characteristic of the chamber: V/AL = 132 for the NBS chamber.
The results obtained were as follows:

| Foam R | Foam A | Foam B |
|---|---|---|
| 175 | 689 | 400 |

Thus it may be seen that a markedly lower fume density was observed in the case of the foam according to the invention than in the case of the foam containing Fyrol.

(f) Toxic products (ppm) evolved during combustion

| | Foam R | Foam A | Foam B |
|---|---|---|---|
| CO | 1,000 | 900 | 320 |
| HCN | 20 | 20 | 12 |

The toxic products evolved were, in the case of the foam of the invention, markedly less than in the case of the reference foam or even in the case of the foam containing Fyrol.

Experiments were also carried out using compound No. 5.

The composition used to prepare the polyurethane foam was as follows:

Alcohol: 80% of TP 440 (trimethylolpropane epoxidised by means of propylene oxide),
isocyanate: 61.6% of TDI (toluene diisocyanate),
blowing agent: 18.8 g of Forane (Freon II),
catalysts: 0.38 g of DBTL (dibutyl-tin dilaurate) and 0.12 g of DABCO (diazabicyclooctane),
silicone: 1.13 g of Si 9193 supplied by Messrs. Rhodorsil; and
flameproofing agent; a phosphonate used in an amount to provide a P content of 0.98%.

The following LOI values were obtained
Reference foam: LOI 0.167
Flameproofed foam: LOI 0.189

It is apparent from all these experiments that the compounds according to the invention can be used as copolycondensed flameproofing additives in rigid polyurethane foams, advantageously in proportions corresponding to phosphorus contents of up to 2%, and preferably of 0.5 to 1.5%, and in particular of approximately 1%.

What is claimed is:

1. A polyurethane foam obtained by reaction of a compound of the formula:

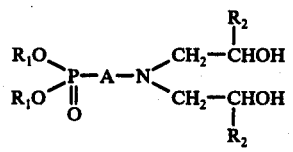

in which $R_1$ is an alkyl group with 1 to 4 carbon atoms, $R_2$ is hydrogen, methyl, or ethyl, and A is $-CH_2-CH_2-CH_2-$, or

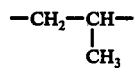

as at least part of the polyol component with a diisocyanate; said reaction is performed in the presence of a pore-forming agent.

2. A foam as claimed in claim 1, in which the amount of said compound is such as to provide a foam having a phosphorus content of from about 0.5 to about 1.5%.

3. The foam according to claim 1 wherein said compound is diethyl 3-[bis-(2-hydroxy-ethyl)-amino]-propyl-phosphonate.

4. The foam according to claim 1 wherein said compound is diethyl 2-[bis-(2-hydroxy-ethyl)-amino]-2-methyl-ethyl-phosphonate.

5. The foam according to claim 1 wherein said compound is diethyl 3-[bis-(2-hydroxy-propyl)-amino] propyl-phosphonate.

6. The foam according to claim 1 wherein said compound is diisopropyl 3-[bis-(2-hydroxy-ethyl)-amino]-propyl-phosphonate.

7. The foam according to claim 1 wherein said compound is diisopropyl 3-[bis-(2-hydroxy-propyl)-amino]-propyl-phosphonate.

* * * * *